(12) United States Patent
Maruyama

(10) Patent No.: US 8,795,722 B2
(45) Date of Patent: Aug. 5, 2014

(54) COMPOSITION FOR COATING COMPRISING LOW-SUBSTITUTED CELLULOSE ETHER AND COATED PREPARATION HAVING UNPLEASANT TASTE MASKED

(75) Inventor: Naosuke Maruyama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 922 days.

(21) Appl. No.: 11/495,124

(22) Filed: Jul. 28, 2006

(65) Prior Publication Data
US 2007/0026063 A1 Feb. 1, 2007

(30) Foreign Application Priority Data
Jul. 29, 2005 (JP) .................................. 2005-220837

(51) Int. Cl.
*A61K 9/20* (2006.01)
*A61K 31/715* (2006.01)

(52) U.S. Cl.
USPC .......................................... 424/464; 514/57

(58) Field of Classification Search
USPC .......................................... 424/464; 514/57
See application file for complete search history.

(56) References Cited

U.S. PATENT DOCUMENTS

| | | | |
|---|---|---|---|
| 4,091,205 A | 5/1978 | Onda et al. | |
| 4,123,403 A * | 10/1978 | Warner et al. | 523/313 |
| 4,258,179 A | 3/1981 | Kawata et al. | |
| 5,409,711 A | 4/1995 | Mapelli et al. | |
| 5,470,581 A | 11/1995 | Grillo et al. | |
| 5,773,031 A * | 6/1998 | Shah et al. | 424/497 |
| 6,022,533 A * | 2/2000 | Goto et al. | 424/78.12 |
| 6,197,348 B1 | 3/2001 | Morella et al. | |
| 6,221,402 B1 | 4/2001 | Itoh et al. | |
| 6,432,448 B1 | 8/2002 | Augello et al. | |
| 6,500,462 B1 | 12/2002 | Augello et al. | |
| 6,709,713 B2 | 3/2004 | Augello et al. | |
| 6,723,342 B1 | 4/2004 | Augello et al. | |
| 2003/0129238 A1 | 7/2003 | Augello et al. | |
| 2003/0166918 A1 | 9/2003 | Obara | |
| 2004/0137043 A1 | 7/2004 | Augello et al. | |

FOREIGN PATENT DOCUMENTS

| | | |
|---|---|---|
| EP | 0 793 959 A1 | 9/1997 |
| EP | 1 103 253 A2 | 5/2001 |
| JP | 53-139715 A | 12/1978 |
| JP | 56-054292 B | 12/1981 |
| JP | 82053100 B | 11/1982 |
| JP | 62-061041 B | 12/1987 |
| JP | 05-508667 A | 2/1993 |
| JP | 95074151 B2 | 8/1995 |
| JP | 09-059147 A | 3/1997 |
| JP | 2836493 B2 | 12/1998 |
| JP | 11-005736 A | 1/1999 |
| JP | 2005009399 W | 7/2000 |
| JP | 2001-055344 A | 2/2001 |
| JP | 3193041 B2 | 7/2001 |
| JP | 2002-204951 * | 7/2002 |
| JP | 2002204951 A | 7/2002 |
| JP | 3350059 B2 | 11/2002 |
| JP | 2003-523934 A | 8/2003 |
| JP | 2003-252902 A | 9/2003 |
| JP | 2005082594 A | 3/2005 |
| KR | 10-2001-0051807 A | 6/2001 |
| KR | 10-2001-0101907 A | 11/2001 |
| WO | WO 89/05635 A | 6/1989 |
| WO | WO 2005/065661 A2 | 7/2005 |

OTHER PUBLICATIONS

European Search Report dated Dec. 6, 2006 for corresponding European Application No. 06253878.0.
Office Action for Japanese Application No. 2005-220837 dated Aug. 10, 2010.
Office Action for Korean Application No. 10-2006-71221 dated Jun. 27, 2013.

* cited by examiner

*Primary Examiner* — Aradhana Sasan
(74) *Attorney, Agent, or Firm* — Alston & Bird LLP

(57) ABSTRACT

The present invention is a composition for coating comprising a wet-milled product obtained by suspending low-substituted cellulose ether having a molar substitution of from 0.05 to 1.0 per anhydrous glucose unit in water and then applying a shear force to the aqueous dispersion. The present invention is also a coated preparation prepared using the composition for coating so as to mask an unpleasant taste and to control a sticky or slimy feel by administration.

16 Claims, No Drawings

COMPOSITION FOR COATING COMPRISING LOW-SUBSTITUTED CELLULOSE ETHER AND COATED PREPARATION HAVING UNPLEASANT TASTE MASKED

FIELD OF THE INVENTION

The present invention relates to a film-coated preparation obtained by covering a solid preparation such as a tablet and a granule serving as pharmaceuticals and health food with low-substituted cellulose ether. In particular, the present invention pertains to a film-coated preparation improved in the masking of an unpleasant taste and giving a less slimy or sticky feel when it is administered.

BACKGROUND OF THE INVENTION

It is already known in the industries such as pharmaceutical, health food and agrichemical industries that a film-forming composition is applied to solid preparations such as tablets and granules. It is applied in order to shield the solid preparations from light, prevent them from oxidation, adhesion and moisture, give them storage stability, sustain the release of a drug, or mask an unpleasant taste or odor.

Examples of the film-forming composition include cellulose derivatives such as water-soluble hydroxypropyl methyl cellulose, hydroxypropyl cellulose, hydroxyethyl cellulose, carboxymethyl cellulose, hydroxyethyl methyl cellulose and hydroxyethyl ethyl cellulose. The other examples include pullulan, carrageenan and polyvinyl alcohol. It is known that coating is carried out by applying an aqueous solution of such a film-forming composition to a preparation.

Hydroxypropyl methyl cellulose having a reduced molecular weight is used widely for coating tablets or granules with water-soluble nonionic cellulose ether. It also exhibits excellent stability as it is left standing so that it has been in wide use mainly as a film-coating agent in recent years. However, preparations coated with such a water-soluble polymer leave an unpleasant taste such as bitterness peculiar to a drug when they are administered as a pharmaceutical or health food because the film easily dissolves in the oral cavity. In addition, the unpleasant taste lowers the compliance of patients with administration. Moreover, administration of preparations coated with a water-soluble base material may give a sticky or slimy feel to patients and therefore become a unpleasant burden to them.

Masking of a bitter taste with a large amount of a sweetener or the like can be given as a method for overcoming such a problem. However, it does not have a sufficient effect. Filling of a drug in a hard capsule can also be given as a countermeasure, but children and the aged encounter difficulty in taking such a drug.

As another method, use of a base material forming a water-insoluble coating film is proposed. Use of a synthetic polymer such as vinyl acetate resins or acrylic resins, or emulsion thereof is provided. However, there is a problem that a monomer remaining in such a synthetic polymer is sometimes toxic or interaction between the monomer and a coated preparation may deteriorate the stability of the film. According to Japanese Patent Application Unexamined Publication (Toku-Hyo) No. 2000-509399, an acrylic resin is used as an example of the synthetic polymer. According to Japanese Patent No. 3193041, an acrylic resin and an enteric cellulose ester are shown as an example of a water-insoluble film. According to Japanese Patent No. 3350059, an acrylic resin is used as a water-insoluble film for an outer layer of granules containing, in the core thereof, a water-swelling polymer.

Use of water-insoluble ethyl cellulose or an enteric base material such as hydroxypropyl methylcellulose phthalate, hydroxypropyl methylcellulose acetate succinate, cellulose acetate phthalate or carboxymethyl ethylcellulose as a cellulose derivative closer to a natural material is proposed in order to solve the above-described problems. When such a base material is used singly, its water insolubility contributes to excellent masking of taste, but decrease in the elution of a drug may prevent the achievement of the intended bioavailability. In addition, since the property of an enteric base material depends on pH, a difference in the pH in the digestive tracts between individuals may lead to uneven elution of a drug. Use of water-insoluble ethyl cellulose is described in Japanese Patent No. 2836493.

As another example, use of a water-insoluble wax, oil or fat, higher alcohol or fatty acid for lowering the elution of a drug is described in Japanese Patent Application Unexamined Publication No. 2005-82594.

An application of a mixture with water-soluble hydroxypropylmethyl cellulose in order to improve the elution is described in Japanese Patent Application Examined Publication No. 7-74151/1995. However, it is difficult to control the mixing and to obtain both good masking of taste and desired elution at the same time. In general, a water-insoluble coating base material is required to be dissolved in an organic solvent prior to application. Accordingly, there is an environmental problem of removing the organic solvent to the air by drying or a problem of a residual solvent in the preparation.

SUMMARY OF THE INVENTION

When a conventional water-soluble polymer is used for coating, the intended masking of an unpleasant taste cannot be realized owing to insufficient water resistance of the coating layer. Use of a water-soluble base material gives a sticky or slimy feel by administration. Use of a conventional water-insoluble base material lowers elution of a drug. In addition, a water-insoluble base material is not suited for aqueous coating. An object of the present invention is to overcome these problems.

Focusing on the various properties of low-substituted cellulose ether which is water-insoluble and swells in water and is soluble in an alkaline solution, the present inventors have conducted an extensive investigation on the use of such a water-swelling base material for forming a film having desired water resistance and permitting excellent elution of a drug without using an organic solvent, and completed the present invention.

In the present invention, there is thus provided a composition for coating comprising a wet-milled product obtained by applying a shear force to an aqueous dispersion of low-substituted cellulose ether having a molar substitution of from 0.05 to 1.0 per anhydrous glucose unit.

A preferable example of the aqueous dispersion of low-substituted cellulose ether may include an aqueous dispersion obtained by suspending and dispersing the low-substituted cellulose ether in water, and an aqueous dispersion obtained by dissolving the low-substituted cellulose ether in an aqueous alkaline solution and neutralizing the resulting aqueous alkaline solution with an acid in an amount equivalent to that of the alkali to precipitate the low-substituted cellulose ether.

A preferable example of a method of applying a shear force to the aqueous dispersion of low-substituted cellulose ether may include a method of causing self-collision of the low-substituted cellulose ether contained in an aqueous dispersion or causing collision of the low-substituted cellulose ether with a collision plate while using a vibratory ball mill, a colloid mill, a homomixer or a homogenizer for milling the low-substituted cellulose ether; a method of spraying an aqueous dispersion of low-substituted cellulose ether from a nozzle at a pressure as high as from 70 to 250 MPa and causing self-collision of the aqueous dispersions of low-substituted cellulose ether or causing collision of the pre-shear aqueous dispersion of low-substituted cellulose ether with a collision plate at an angle of from 90 to 180° from 1 to 200 times, thereby reducing the average particle size of the low-substituted cellulose ether to one-fourth or less of that before the application of a shear force; and a method of applying a shear force of 500 sec−1 or greater to an aqueous dispersion of low-substituted cellulose ether from 1 to 60 times for milling and dispersing the low-substituted cellulose ether.

The composition for coating of the present invention can be obtained preferably by dissolving low-substituted cellulose ether in an aqueous alkaline solution and neutralizing the resulting solution with an acid in an amount equivalent to that of the alkali while shearing the alkaline solution in a colloid mill for milling the low-substituted cellulose ether or conducting collision and pulverization of the low-substituted cellulose ether in a homogenizer.

In the present invention, there is also provided a coated solid preparation obtained by applying the above-described film composition for coating to a solid preparation containing a drug.

Coating a preparation with composition of the present invention can provide a coated solid preparation permitting excellent elution of a drug, having a high masking effect of an unpleasant taste or the like of the drug, and giving an excellent feel upon ingestion without a sticky or slimy feel when the preparation is administered.

DETAILED DESCRIPTION OF THE PREFERRED EMBODIMENTS

The low-substituted cellulose ether of the present invention is water-insoluble and swells in water, and is soluble in an aqueous alkaline solution.

Celluloses are usually insoluble in water, but become soluble when the hydrogen atom of the hydroxyl group of the glucose ring of the celluloses is substituted with an alkyl or hydroxyalkyl group. The solubility depends on the substitution degree. Celluloses having a low degree of substitution are water-insoluble and swell in water, and are soluble in an aqueous alkaline solution.

Typical low-substituted cellulose ether to be used in the present invention can have a molar substitution of preferably from 0.05 to 1.0, more preferably from 0.1 to 0.8. The cellulose ether which is insoluble in water and produces a dispersion having high stability by application of a shear force may be used. When the molar substitution is less than 0.05, a stable dispersion may not be obtained by the application of a shear force. When the molar substitution is more than 1.0, water solubility of the cellulose ether may increase and masking of an unpleasant taste may be lowered. Examples of such low-substituted cellulose ether may include low-substituted alkyl cellulose such as low-substituted methyl cellulose and low-substituted ethyl cellulose, low-substituted hydroxyalkyl cellulose such as low-substituted hydroxyethyl cellulose and low-substituted hydroxypropyl cellulose, and low-substituted hydroxyalkyl alkyl cellulose such as low-substituted hydroxypropyl methyl cellulose, low-substituted hydroxyethyl methyl cellulose and low-substituted hydroxyethyl ethyl cellulose. Of these, low-substituted hydroxypropyl cellulose may be especially preferred.

Such low-substituted cellulose ether is water-insoluble and swells with absorbed water, and soluble in an aqueous alkaline solution. Low-substituted hydroxypropyl cellulose is a typical example and now commercially available as a trade name of L-HPC from Shin-Etsu Chemical Co., Ltd. It is listed in the Japanese Pharmacopoeia and generally incorporated as a disintegrant or binder in tablets or granules particularly in the field of pharmaceutical materials.

The methods for preparing the low-substituted cellulose ether are known and described, for example, in Japanese Patent Application Examined Publication No. 57-53100/1982.

First, alkali cellulose can prepared by immersing pulp, which is a starting material, in an aqueous alkaline solution such as sodium hydroxide; by mixing pulverized pulp with an alkaline solution; or by dispersing pulp powders in an organic solvent and then adding an alkali to the resulting dispersion.

The alkali cellulose thus obtained is then charged in a reactor and an etherifying agent such as propylene oxide or ethylene oxide is added therein. The resulting mixture may be heated for reaction to yield the corresponding cellulose ether.

After completion of the reaction, the resulting crude cellulose ether may be transferred to another tank, in which the alkali is neutralized with an acid. The resulting solid can be washed, dried and pulverized to yield a finished product in the powder form.

Alternately, it may be also obtained by dissolving the crude cellulose ether just after the reaction in water completely or partially, neutralizing the resultant, collecting the polymer thus precipitated, washing, drying and then pulverizing the polymer.

The composition for coating of the present invention can be prepared, for example, by wet-milling the low-substituted cellulose ether thus obtained. More specifically, a dispersion of the low-substituted cellulose ether can be obtained by suspending and dispersing it in water; or by dissolving it once in an aqueous alkaline solution, neutralizing the solution to cause precipitation, and then suspending and dispersing the precipitate. Subsequently, a shear force can be applied to the dispersion to cause self-collision of the low-substituted cellulose ether or cause collision of it with a collision plate. In the present invention, the dispersion of low-substituted cellulose ether prior to application of a shear force may be called "pre-shear dispersion", while that after application of a shear force may be called "sheared dispersion"

The method for preparing a pre-shear dispersion of low-substituted cellulose ether by dissolving the low-substituted cellulose ether once in an aqueous alkaline solution and then neutralizing the solution to cause precipitation may comprise dispersing the low-substituted cellulose ether in water; or dissolving the low-substituted cellulose ether in an aqueous solution of an alkali such as sodium hydroxide or potassium hydroxide (having an alkali concentration of typically from 2 to 25% by weight, especially from 3 to 15% by weight) and then neutralizing the resulting solution with an equivalent amount of an acid to precipitate the low-substituted cellulose ether.

The sheared dispersion to be used for the composition for coating can be obtained, for example, by causing self-collision of the dispersed low-substituted cellulose ether or causing collision of it with a collision plate for milling it. An apparatus for preparing the sheared dispersion of low-substituted cellulose ether by causing self-collision of the low-substituted cellulose ether or causing collision of it with a collision plate for milling it may include, but not limited to, a vibratory ball mill, a colloid mill, a homomixer and a homogenizer. Specific examples of the colloid mill may include "Masscolloider" and "Cerendipitor" (trade names; products of Masuko Sangyo Co., Ltd.). Preferable examples of the homogenizer which can prepare a uniform dispersion may include "Homogenizer" (product of Sanwa Machine Co., Inc.) which is a high pressure homogenizer capable of spraying a treatment fluid through openings of a valve under high pressure and thereby causing collision and friction of the low-substituted cellulose ethers, "Ultimaizer System" (trade name; product of Sugino Machine Co., Ltd.), "Microfluidizer" (trade name; product of Mizuho Kogyo Co., Ltd.), "High pressure homogenizer" (product of Gaulin Co., Ltd.), and ultrasonic homogenizers utilizing oscillation of an ultrasonic wave and "Ultrasonic Homogenizer" (trade name; product of Nissei Corporation). A sheared dispersion which has been subjected to repeated treatments with such an apparatus can also be employed.

Further, a method for preparing the sheared dispersion of low-substituted cellulose ether may comprise dissolving the low-substituted cellulose ether in an aqueous alkaline solution (having an alkali concentration of typically from 2 to 25% by weight, especially from 3 to 15% by weight) and neutralizing the alkaline solution with an amount equivalent to that of the alkali of an organic acid such as acetic acid, formic acid or propionic acid, or of an inorganic acid such as hydrochloric acid or sulfuric acid, while shearing and milling the resulting alkaline solution in a colloid mill or causing collision and pulverization of the low-substituted cellulose ether in the homogenizer, as described in Japanese Patent Application Unexamined Publication No. 2002-204951.

When the sheared dispersion of low-substituted cellulose ether is prepared, it may be effective to spray the pre-shear dispersion of low-substituted cellulose ether from a pair of nozzles to cause them to collide each other or to spray the pre-shear dispersion of low-substituted cellulose ether from a nozzle to a collision plate for causing the dispersion to collide with a collision plate. During the collision, it may be desired to adjust the spray pressure of the pre-shear dispersion of low-substituted cellulose ether from the nozzle to from 70 to 250 MPa and the self-collision angle of the pre-shear dispersion of low-substituted cellulose ether or the collision angle of the pre-shear dispersion of low-substituted cellulose ether against a collision plate to from 90 to 180°, more preferably from 95 to 178°, still more preferably from 100 to 170°. The frequency of the collision may be preferably from 1 to 200 times, especially preferably from 5 to 120 times. The average particle size of the low-substituted cellulose ether may be reduced by the collision to preferably not greater than 1/4, more preferably from 1/5 to 1/100, still preferably from 1/6 to 1/50, especially preferably from 1/7 to 1/20 of the average particle size of the low-substituted cellulose ether prior to collision. The average particle size can be determined by a photograph made through an optical microscope, a polarization microscope or a transmission electron microscope, or determined as an average of the lengths of at least 200 particles measured by an image analyzer. A sufficiently uniform dispersion of low-substituted cellulose ether cannot be obtained when the pressure, collision angle or collision frequency is outside the above-described range and in such a case, a remarkable reduction in the molecular weight of the low-substituted cellulose ether may occur.

When the low-substituted cellulose ether is dispersed with milling, it may be preferable to apply a shear force of from 500 sec−1 or greater, more preferably 1000 sec−1 or greater, still more preferably 1500 sec−1 or greater to the dispersion. The shear force may be applied repeatedly or continuously. It may be preferably applied preferably from 1 to 60 times, more preferably from 10 to 60 times in order to attain sufficient milling. When the shear force is applied less than once, the resulting low-substituted cellulose ether may have a deteriorated film forming property. When the shear force is applied more than 60 times, the polymerization of the low-substituted cellulose ether may decrease, leading to reduction in the film strength.

The dispersion of low-substituted cellulose ether thus obtained can have a concentration of preferably from 0.5 to 10% by weight, especially preferably from 1 to 5% by weight. When the concentration is less than 0.5% by weight, it takes long hours to obtain a desired coating weight when the low-substituted cellulose ether is used later for coating, which may lead to a decrease in the productivity. When the concentration is more than 10% by weight, the viscosity of the wet-milled product may increase excessively so that the delivery of it may be disturbed.

In addition, a method for obtaining a uniformly milled product by adding an acid to an alkaline solution of low-substituted cellulose ether to cause neutralization and precipitation while mixing in a high-speed stirrer is disclosed in Japanese Patent Application Unexamined Publication No. 2002-204951. In this method, wet-milling may be conducted after adding the acid to the alkaline solution of low-substituted cellulose ether for neutralization and precipitation, and washing the resulting gelled product with hot water or the like. In the above method, similar results can be obtained either by dissolving the low-substituted cellulose ether powders obtained as the final product in an aqueous alkaline solution or by dissolving crude cellulose ether containing alkali in water just after the reaction. In the latter case, since the crude cellulose ether contains alkali, a solvent used for dissolving it therein can be only water. However, an alkali may be added to attain complete dissolution. The present invention can be suitable in either case.

Examples of the alkali to be used for dissolving the low-substituted cellulose ether may include potassium hydroxide and sodium hydroxide. The concentration of the alkali can be determined appropriately, depending on a type of substitution or a substitution degree of the cellulose ether. The preferable concentration may be typically from 2 to 25% by weight, especially from 3 to 15% by weight. As a typical example, a 7 to 10% by weight solution of sodium hydroxide can be used for low-substituted hydroxypropyl cellulose having a molar substitution of 0.2. The solution may be transparent or incompletely transparent, depending on the difference in distribution of substituents. In the latter case, when an apparent increase in viscosity is observed, the low-substituted cellulose ether is regarded to be dissolved in the alkaline solution.

Examples of the acid to be used for neutralization may include organic acid such as acetic acid, formic acid and propionic acid and inorganic acid such as hydrochloric acid and sulfuric acid. Although its concentration can be selected freely, from 5 to 10% by weight may be preferred.

The concentration of the low-substituted cellulose ether when it is subjected to milling may be preferably from 0.5 to 10% by weight. When the concentration is less than 0.5% by weight, it may take long hours to obtain a desired coating weight, leading to a decrease in productivity. When the concentration is more than 10% by weight, it may become impossible to perform coating because milling of the slurry results in a gel or sol having high viscosity.

The average particle size of the low-substituted cellulose ether in the wet-milled product can be determined from a photograph made through an optical microscope, polarization microscope or transmission electron microscope, or determined by measuring lengths of at least 200 particles with an image analyzer. It may be preferably 20 μm or less, especially preferably 10 μm or less. When the average particle size is more than 20 μm, drying of the aqueous dispersion may produce a discontinuous film which is partially transparent or a film comprising deposition of powders. The film comprising deposition of powders has weak film strength at the time of drying, cannot keep its shape when wetted with water, and cannot fulfill the object of the present invention, that is, taste masking. The lower limit of the average particle size may be, but not limited to, approximately 1 μm.

It is conventionally known that the particle size in an aqueous dispersion of a water-insoluble polymer has an influence on the film-forming property after drying. This also applies to the milled product of the low-substituted cellulose ether. When the particle size in an aqueous dispersion is smaller, the closer packing can be attained when the dispersion is dried. This causes coalescence of adjacent particles, facilitating the formation of a transparent continuous film.

The continuous transparent film has high strength at the time of drying, is insoluble in water, and swells with absorbed water. Such properties are considered to contribute masking of an unpleasant taste. The low-substituted cellulose ether has been used as a disintegrant because of the property of swelling with adsorbed water. Compared with the other water-insoluble film such as ethyl cellulose or acrylic resin film, the low-substituted cellulose ether film absorbs much water and disintegrates by swelling after certain hours. Thus, this film is considered to have a property for smoothly releasing a drug.

A plasticizer such as glycerin, propylene glycol, polyethylene glycol, triethyl citrate, or mono-, di- or tri-acetin may be optionally added to the coating composition of the present invention. It may be especially preferred that at least one substance selected from the group consisting of glycerin, propylene glycol and polyethylene glycol is added. Addition of the plasticizer may be effective for improving the film-forming property and improving the flexibility of the resulting film. The amount of the plasticize may be preferably from about 5 to 50% by weight based on the amount of the low-substituted cellulose ether. When the amount is less than 5% by weight, a film having flexibility may not be obtained. When the amount is more than 50% by weight, the water resistance of the resulting film may be lowered.

Further, an adhesion preventive such as talc and silica can be added. A cellulose derivative including hydroxypropyl methyl cellulose, hydroxypropyl cellulose, hydroxyethyl cellulose, carboxymethyl cellulose, hydroxyethyl methyl cellulose and hydroxyethyl ethyl cellulose, pullulan, carrageenan, polyvinyl alcohol, sugar or sugar alcohol can be added for adjusting the solubility.

The concentration of the low-substituted cellulose ether in the coating composition of the present invention may be preferably from 1 to 10% by weight, more preferably from 3 to 6% by weight. When the amount is less than 1% by weight, it may take long hours to obtain a desired coating amount, leading to a reduction in productivity. When the amount is more than 10% by weight, the viscosity of the wet-milled product may become too high to deliver the coating composition.

Examples of the solid preparation to be used for coating may include tablets, granules, fine granules, powders and pills.

A coater may include, but not limited to, a draft coating pan, a fluid bed granulating coater, a rolling fluid-bed coater, and a high-speed agitation granulator. The coating can be carried out under conventional operation conditions.

The coating can be typically carried out by simultaneously spraying a coating solution and drying in a coater. In this case, further drying can be conducted in the coater after completion of the coating if necessary.

The present invention is suited for drugs having a particularly unpleasant taste or stimulating the oral cavity. Examples of such drugs may include, but not limited to, ibuprofen, dicrofenac sodium, acetylsalicylic acid, parasetamol, cimetidine, carboxymethylcysteine, tiopronin, dextromethorphan hydrobromide, codeine and salts thereof, buflomedil, morphine and salts thereof, 5-aminosalicylic acid, penicillin and derivatives thereof, erythromycin and derivatives thereof, cephalosporin, tetracycline, and crude drugs such as *ginkgo biloba* extract.

The coating weight of the low-substituted cellulose ether can vary, depending on its preparation form. The coating weight of the low-substituted cellulose ether may be preferably from about 1 to 30 parts by weight, especially preferably from 1 to 10 parts by weight based on 100 parts by weight of an uncoated solid preparation. When the coating weight is less than 1 part by weight, the intended masking of taste may not be achieved. When the coating weight is more than 30 parts by weight, the elution of a drug may be lowered.

The present invention will hereinafter be described in detail based on Examples. However, it should not be construed that the present invention is limited to or by Examples.

REFERENCE EXAMPLE

Preparation of Raw Tablets

Powders which will be described below except magnesium stearate (lubricant) were charged in a V-mixer having an inner volume of 5 L and mixed for 10 minutes. Magnesium stearate was then added to the resulting mixture, followed by mixing for 1 minute to prepare powders to be tableted. The resulting powders were charged in a hopper of a rotary tableting machine and raw tablets having a tablet weight of 200 mg, tablet diameter of 8 mm, and a curved radius of 6.5 mm were formed continuously under the conditions of main compression pressure of 1 t, precompression pressure of 0.3 t, and rotation speed of 20 rpm.

Composition:

| | | |
|---|---|---|
| *Ginkgo biloba* extract | 200 g | 20 parts by weight |
| Spray dried lactose | 600 g | 60 parts by weight |
| Low-substituted hydroxypropyl cellulose (LH-21) | 200 g | 20 parts by weight |
| Magnesium Stearate | 10 g | 1 part by weight |
| Hardness of the resulting raw tablet: | | 7.1 kg, |
| Disintegration time: | | 15 minutes |

Disintegration time was evaluated using the test solution of 37° C. and pure water in accordance with the disintegration test method specified in the Japanese Pharmacopoeia.

Six healthy adult volunteers were asked to place a tablet on their tongue in the oral cavity and time until they felt a bitter taste was measured. As a result, any of these volunteers felt a strong bitter taste within two seconds.

Example 1

After 50 g of low-substituted hydroxypropyl cellulose powder (having a molar substitution of 0.2 per anhydrous glucose unit) was dispersed in 950 g of pure water, the resulting dispersion was treated by a wet high-pressure dispersing and grinding machine "Ultimaizer" (trade name; product of Sugino Machine Limited) ten times under a pressure of 150 MPa to yield an aqueous dispersion in the cream form. An average particle size of the low-substituted hydroxypropyl cellulose in the aqueous dispersion was measured to be 6 μm. Pure water (400 g) was added to 600 g of the aqueous dispersion and they were mixed into a uniform mixture by stirring, whereby a coating composition was prepared.

Under the below-described conditions, the resulting coating composition was applied in an amount of up to 3 parts by weight, in terms of the amount of low-substituted cellulose ether, to 100 parts by weight of the raw tablet prepared in Reference Example. Organoleptic evaluation of the tablets thus coated was performed. A tablet was placed on the tongue in the oral cavity of each of six healthy adult volunteers. Time until they felt a bitter taste and the feeling in the oral cavity brought by the administration are described in Tables 1 and 2, respectively. The evaluation results of the disintegration time of the coated tablet in pure water in accordance with the disintegration test method specified in the Japanese Pharmacopoeia are shown in Table 3.

Coating Conditions
  Apparatus: Draft pan coater (inner diameter: 30 cm)
  Charged amount: 1 kg
  Intake air temperature: 80° C.
  Outtake air temperature: 48 to 51° C.
  Intake air amount: 1 m3/min
  Rotation speed of pan: 18 rpm
  Spraying rate: 6 g/min
  Spraying air pressure: 150 kPa Example 2

To 600 g of an aqueous dispersion prepared in the same manner as that in Example 1 were added 6 g of glycerin and 394 g of pure water, followed by mixing with stirring until the mixture became uniform, whereby a composition for coating was prepared. In the same manner as that in Example 1, the resulting composition for coating was applied in an amount of up to 3 parts by weight, in terms of the amount of low-substituted cellulose ether, to 100 parts by weight of the raw tablet prepared in Reference Example. An organoleptic evaluation of the tablets thus coated was performed. A tablet was placed on the tongue in the oral cavity of each of six healthy adult volunteers. Time until they felt a bitter taste and the feeling in the oral cavity brought by the administration are described in Tables 1 and 2, respectively. The evaluation results of the disintegration time of the coated tablet in pure water in accordance with the disintegration test method specified in the Japanese Pharmacopoeia are shown in Table 3.

Example 3

In the same manner to that in Example 1 except use of low-substituted methyl cellulose powder (having a molar substitution of 0.28 per anhydrous glucose unit) instead of the low-substituted hydroxypropyl cellulose powder, an aqueous dispersion was obtained. The average particle size of the low-substituted methyl cellulose in the aqueous dispersion measured 10 μm. To 600 g of the resulting aqueous dispersion were added 6 g of glycerin and 394 g of pure water, followed by mixing with stirring until the mixture became uniform.

Under the same condition as that in Example 1, the resulting composition for coating was applied in an amount of up to 3 parts by weight, in terms of the amount of low-substituted cellulose ether, to 100 parts by weight of the raw tablet prepared in Reference Example. An organoleptic evaluation of the tablets thus coated was performed. The tablet was placed on the tongue in the oral cavity of each of six healthy adult volunteers. Time until they felt a bitter taste and the feeling in the oral cavity brought by the administration are described in Tables 1 and 2, respectively. The evaluation results of the disintegration time of the coated tablet in pure water in accordance with the disintegration test method specified in the Japanese Pharmacopoeia are shown in Table 3.

Example 4

In the same manner as that in Example 1 except use of low-substituted hydroxypropyl methyl cellulose powder (having a molar substitution of a methoxyl group of 0.13 and a molar substitution of a hydroxypropoxyl group of 0.18 per anhydrous glucose unit) instead of the low-substituted hydroxypropyl cellulose powder, an aqueous dispersion was obtained. The average particle size of the low-substituted methyl cellulose in the aqueous dispersion measured 8 μm. To 600 g of the resulting aqueous dispersion were added 6 g of glycerin and 394 g of pure water, followed by mixing with stirring until the mixture became uniform.

Under the same condition as that in Example 1, the resulting composition for coating was applied in an amount of up to 3 parts by weight, in terms of the amount of low-substituted cellulose ether, to 100 parts by weight of the raw tablet prepared in Reference Example. An organoleptic evaluation of the tablets thus coated was performed. The tablet was placed on the tongue in the oral cavity of each of six healthy adult volunteers. Time until they felt a bitter taste and the feeling in the oral cavity brought by the administration are described in Tables 1 and 2, respectively. The evaluation results of the disintegration time of the coated tablet in pure water in accordance with the disintegration test method specified in the Japanese Pharmacopoeia are shown in Table 3.

Comparative Example 1

In the same manner as in Example 1, 500 g of an aqueous 6% by weight solution of water-soluble hydroxypropyl methyl cellulose (having a molar substitution of a methoxyl group of 1.9 and that of a hydroxypropoxyl group of 0.24, each per anhydrous glucose unit) was applied in an amount of up to 3 parts by weight, in terms of low-substituted cellulose ether, to 100 parts by weight of the raw tablets prepared in Reference Example. An organoleptic evaluation of the tablets thus coated was performed. The tablet was placed on the tongue in the oral cavity of each of six healthy adult volunteers. Time until they felt a bitter taste and the feeling in the oral cavity brought by the administration are described in Tables 1 and 2, respectively. The evaluation results of the disintegration time of the coated tablet in pure water in accordance with the disintegration test method specified in the Japanese Pharmacopoeia are shown in Table 3.

TABLE 1

| | Time until volunteer felt bitter taste (seconds) | | | | | |
|---|---|---|---|---|---|---|
| | Example 1 | Example 2 | Example 3 | Example 4 | Comp. Ex. 1 | Ref. Ex. |
| Volunteer A | 40 | 60 | 55 | 58 | 5 | 1 |
| Volunteer B | 100 | 135 | 78 | 89 | 10 | 2 |
| Volunteer C | 51 | 80 | 45 | 60 | 7 | 1 |
| Volunteer D | 60 | 65 | 58 | 55 | 6 | 1 |
| Volunteer E | 61 | 63 | 60 | 58 | 5 | 1 |
| Volunteer F | 80 | 100 | 92 | 72 | 8 | 1 |

* The raw tablet without coating of Example 1 was used

TABLE 2

Feeling evaluation in oral cavity by administration

|  | Example 1 | Example 2 | Example 3 | Example 4 | Comp. Ex. 1 |
|---|---|---|---|---|---|
| Volunteer A | Good | Good | Good | Good | Poor |
| Volunteer B | Good | Good | Good | Good | Poor |
| Volunteer C | Good | Good | Good | Good | Poor |
| Volunteer D | Good | Good | Good | Good | Poor |
| Volunteer E | Good | Good | Good | Good | Poor |
| Volunteer F | Good | Good | Good | Good | Poor |

Good: neither sticky feeling nor slimy feeling
Poor: sticky and slimy feeling

TABLE 3

|  | Disintegration Time (minutes) |
|---|---|
| Example 1 | 18 |
| Example 2 | 19 |
| Example 3 | 21 |
| Example 4 | 18 |
| Comp. Ex. 1 | 16 |
| Ref. Ex. 1* | 15 |

*The raw tablet without coating of Example 1 was used.

It has been found that compared with tablets coated with a conventional water-soluble polymer (Comparative Example 1), the tablets coated with the coating composition of the present invention have a high masking effect of an unpleasant taste. In addition, the tablets coated with the coating composition coating of the present invention leave an excellent feeling after administration without causing a sticky or slimy feel. Moreover, there was almost no difference in the disintegration time between the coated tablets of the present invention and un-coated tablets. Since the low-substituted cellulose ether of the present invention has properties of being insoluble in water and swelling with absorbed water and a film obtained from it also has these properties, a film of the coated tablet disintegrates by swelling with absorbed water, leading to elution of the drug.

The invention claimed is:

1. A coating composition, consisting essentially of a wet-milled product obtained by applying a shear force to an aqueous dispersion of low-substituted cellulose ether powder that is water-insoluble and water-swelling, wherein said aqueous dispersion of low-substituted cellulose ether powder is obtained by suspending and dispersing the low-substituted cellulose ether powder in water and said low-substituted cellulose ether powder having a molar substitution of from 0.05 to 1.0 per anhydrous glucose unit and acting as a continuous transparent film-forming element, wherein said low-substituted cellulose ether powder in the wet-milled product has an average particle size of 20 μm or less, and the composition is in a form adapted for coating solid preparations, wherein the solid preparations are tablets or granules.

2. The coating composition according to claim 1, further consisting essentially of at least one plasticizer selected from the group consisting of glycerin, propylene glycol and polyethylene glycol.

3. The coating composition according to claim 1, wherein said applying the shear force to the aqueous dispersion of low-substituted cellulose ether comprises causing self-collision of the low-substituted cellulose ether contained in the aqueous dispersion or causing collision of the low-substituted cellulose ether with a collision plate by a vibratory ball mill, colloid mill, homomixer or homogenizer for milling the low-substituted cellulose ether.

4. The coating composition according to claim 1, wherein said applying the shear force to the aqueous dispersion of low-substituted cellulose ether comprises spraying the aqueous dispersion of low-substituted cellulose ether from a nozzle at a high pressure of from 70 to 250 MPa for causing self-collision of the aqueous dispersions of low-substituted cellulose ether or causing collision of the aqueous dispersion of low-substituted cellulose ether with a collision plate from 1 to 200 times at an angle of from 90 to 180°, thereby reducing an average particle size of the low-substituted cellulose ether by one-fourth or less.

5. The coating composition according to claim 1, wherein said applying the shear force to the aqueous dispersion of low-substituted cellulose ether comprises applying a shear rate of 500 sec-1 or greater to the aqueous dispersion of low-substituted cellulose ether from 1 to 60 times for milling and dispersing the low-substituted cellulose ether.

6. A coated solid preparation obtained by applying a coating composition to a solid preparation containing a drug, said coating composition consisting essentially of a wet-milled product obtained by applying a shear force to an aqueous dispersion of low-substituted cellulose ether powder that is water-insoluble and water-swelling, wherein said aqueous dispersion of low-substituted cellulose ether powder is obtained by suspending and dispersing the low-substituted cellulose ether powder in water and said low-substituted cellulose ether powder having a molar substitution of from 0.05 to 1.0 per anhydrous glucose unit and acting as a continuous transparent film-forming element, wherein said low-substituted cellulose ether powder in the wet-milled product of the coating composition has an average particle size of 20 μm or less, and the composition is in a form adapted for coating solid preparations, wherein the solid preparations are tablets or granules.

7. The coated solid preparation according to claim 6, wherein the coating composition further consisting essentially of at least one plasticizer selected from the group consisting of glycerin, propylene glycol and polyethylene glycol.

8. The coated solid preparation according to claim 6, wherein, in said coating composition, said applying the shear force to the aqueous dispersion of low-substituted cellulose ether comprises causing self-collision of the low-substituted cellulose ether contained in the aqueous dispersion or causing collision of the low-substituted cellulose ether with a collision plate by a vibratory ball mill, colloid mill, homomixer or homogenizer for milling the low-substituted cellulose ether.

9. The coated solid preparation according to claim 6, wherein, in said coating composition, said applying the shear force to the aqueous dispersion of low-substituted cellulose ether comprises spraying the aqueous dispersion of low-substituted cellulose ether from a nozzle at a high pressure of from 70 to 250 MPa for causing self-collision of the aqueous dispersions of low-substituted cellulose ether or causing collision of the aqueous dispersion of low-substituted cellulose ether with a collision plate from 1 to 200 at an angle of from 90 to 180°to, thereby reducing an average particle size of the low-substituted cellulose ether by one-fourth or less.

10. The coated solid preparation according to claim 6, wherein, in said coating composition, said applying the shear force to the aqueous dispersion of low-substituted cellulose ether comprises applying a shear rate of 500 sec-1 or greater to the aqueous dispersion of low-substituted cellulose ether from 1 to 60 times for milling and dispersing the low-substituted cellulose ether.

11. The coating composition according to claim 1, wherein the composition is devoid of water-soluble cellulose.

12. The coated solid preparation according to claim 6, wherein the composition is devoid of water-soluble cellulose.

13. The coating composition according to claim 1, wherein the coating composition consists of a wet-milled product obtained by applying a shear force comprising a shear rate of $500 sec^{-1}$ to $1500 sec^{-1}$ to an aqueous dispersion of low-substituted cellulose ether that is water-insoluble and water-swelling, said low-substituted cellulose ether having a molar substitution of from 0.05 to 1.0 per anhydrous glucose unit, wherein said low-substituted cellulose ether in the wet-milled product has an average particle size of 20 μm or less, and the composition is in a form adapted for coating solid preparations, wherein the solid preparations are tablets or granules.

14. The coated solid preparation according to claim 6, wherein the coating composition consists of a wet-milled product obtained by applying a shear force comprising a shear rate of $500 sec^{-1}$ to $1500 sec^{-1}$ to an aqueous dispersion of low-substituted cellulose ether that is water-insoluble and water-swelling, said low-substituted cellulose ether having a molar substitution of from 0.05 to 1.0 per anhydrous glucose unit, wherein said low-substituted cellulose ether in the wet-milled product has an average particle size of 20 μm or less, and the composition is in a form adapted for coating solid preparations, wherein the solid preparations are tablets or granules.

15. The coating composition according to claim 1, wherein said coating composition is a transparent continuous film.

16. The coated solid preparation according to claim 6, wherein said coating composition is a transparent continuous film.

\* \* \* \* \*

UNITED STATES PATENT AND TRADEMARK OFFICE
CERTIFICATE OF CORRECTION

| | |
|---|---|
| PATENT NO. | : 8,795,722 B2 |
| APPLICATION NO. | : 11/495124 |
| DATED | : August 5, 2014 |
| INVENTOR(S) | : Maruyama |

Page 1 of 1

It is certified that error appears in the above-identified patent and that said Letters Patent is hereby corrected as shown below:

In the claims:

Column 12, Claim 9
Line 58, "1 to 200" should read --1 to 200 times--;
Line 59, "90 to 180°to" should read --90 to 180°--.

Signed and Sealed this
Second Day of December, 2014

Michelle K. Lee
*Deputy Director of the United States Patent and Trademark Office*